(12) United States Patent
Larose et al.

(10) Patent No.: US 10,441,693 B2
(45) Date of Patent: Oct. 15, 2019

(54) AXIAL FLOW BLOOD PUMP WITH RADIALLY OFFSET ROTOR

(71) Applicant: HeartWave, Inc., Miami Lakes, FL (US)

(72) Inventors: Jeffrey A. Larose, Sunrise, FL (US); Carlos Reyes, Davie, FL (US); Charles R. Shambaugh, Coral Gables, FL (US)

(73) Assignee: HeartWare, Inc., Miami Lakes, FL (US)

(*) Notice: Subject to any disclaimer, the term of this patent is extended or adjusted under 35 U.S.C. 154(b) by 47 days.

(21) Appl. No.: 15/475,432

(22) Filed: Mar. 31, 2017

(65) Prior Publication Data

US 2017/0281842 A1  Oct. 5, 2017

Related U.S. Application Data

(60) Provisional application No. 62/316,729, filed on Apr. 1, 2017.

(51) Int. Cl.
*A61M 1/10* (2006.01)
*A61M 1/12* (2006.01)

(52) U.S. Cl.
CPC .......... *A61M 1/1036* (2014.02); *A61M 1/101* (2013.01); *A61M 1/1008* (2014.02); *A61M 1/1015* (2014.02); *A61M 1/1017* (2014.02); *A61M 1/122* (2014.02)

(58) Field of Classification Search
CPC ........ F16C 39/00; F16C 39/06; F16C 39/063; A61M 1/10; A61M 1/101; A61M 1/1015; A61M 1/1031; A61M 1/122; H02K 7/14; H02K 7/09; H02K 5/12; H02K 41/03; H02K 5/128; H02K 5/1285; Y10S 415/90
USPC .............................. 417/423.7; 604/131, 151
See application file for complete search history.

(56) References Cited

U.S. PATENT DOCUMENTS

| | | | |
|---|---|---|---|
| 5,507,629 A | 4/1996 | Jarvik | |
| 5,840,070 A * | 11/1998 | Wampler | F16C 39/063 604/131 |
| 6,264,635 B1 | 7/2001 | Wampler et al. | |
| 7,976,271 B2 | 7/2011 | LaRose et al. | |
| 8,007,254 B2 | 8/2011 | LaRose et al. | |
| 2007/0100196 A1 * | 5/2007 | LaRose | A61M 1/101 600/16 |
| 2015/0051438 A1 | 2/2015 | Taskin | |

FOREIGN PATENT DOCUMENTS

WO   2010029296 A2   3/2010

OTHER PUBLICATIONS

International Search Report and Written Opinion dated Jun. 28, 2017 for International Application No. PCT/US2017/025283, International Filing Date—Mar. 31, 2017 consisting of 10-pages.

* cited by examiner

*Primary Examiner* — Jon Eric C Morales

(74) *Attorney, Agent, or Firm* — Christopher & Weisberg, P.A.

(57) ABSTRACT

A blood pump including a housing defining a proximal end, a distal end, and a first axis extending from the proximal end to the distal end. A ferromagnetic rotor is disposed within the housing and configured pump blood in a direction along the first axis. A stator is disposed within housing and around the ferromagnetic rotor, the stator is configured to apply a magnetic force causing rotation of the ferromagnetic rotor, the stator being eccentric to the rotor.

16 Claims, 4 Drawing Sheets

AXIAL FLOW BLOOD PUMP WITH RADIALLY OFFSET ROTOR

CROSS-REFERENCE TO RELATED APPLICATION

This application is related to and claims priority to U.S. Provisional Patent Application Ser. No. 62/316,729, filed Apr. 1, 2016, entitled AXIAL FLOW BLOOD PUMP WITH RADIALLY OFFSET ROTOR, the entirety of which is incorporated herein by reference.

STATEMENT REGARDING FEDERALLY SPONSORED RESEARCH OR DEVELOPMENT n/a

TECHNICAL FIELD

The present disclosure relates to liquid pumps and particularly to blood pumps that are used as components of mechanical circulatory support devices ("MCSDs").

BACKGROUND

MCSDs are commonly used to assist the pumping action of a failing heart. Typically, an MCSD includes an implantable blood pump that is surgically implanted in the patient's body. The MCSD has a housing with an inlet and an outlet and has a rotor mounted within the housing. The inlet of the housing is connected to a chamber of the patient's heart, typically the left ventricle, whereas the outlet is connected to an artery such as the aorta. Rotation of the rotor drives the blood from the inlet towards the outlet and thus assists flow from the chamber of the heart into the artery.

Blood pumps used in MCSDs desirably are provided with contactless bearings so that, in operation, the rotor floats within the housing. With contactless bearings, there is no solid-to-solid contact between the rotor and the housing and thus no mechanical wear during operation. One form of contactless bearing is a hydrodynamic bearing. As further discussed below, in a hydrodynamic bearing, the liquid being pumped passes between a surface of the rotor and a surface of the clearance between the surfaces of a hydrodynamic bearing is many times larger than the dimensions of blood cells. However, in some cases the blood passing through the pump may contain particles of thrombus, a solid or semi-solid deposit generated within the patient's body. The thrombus can lodge on a surface of the hydrodynamic bearing and impede its operation. The surfaces are configured so that as the rotor turns, the fluid disposed between these surfaces exerts pressure on the surface of the rotor that holds the rotor away from the housing.

SUMMARY

The present invention advantageously provides for a blood pump including a housing defining a proximal end, a distal end, and a first axis extending from the proximal end to the distal end. A ferromagnetic rotor is disposed within the housing and configured pump blood in a direction along the first axis. A stator is disposed within housing and around the ferromagnetic rotor, the stator is configured to apply a magnetic force causing rotation of the ferromagnetic rotor, the stator being eccentric to the rotor.

In another aspect of this embodiment, a non-ferromagnetic tubular body is disposed between the rotor and the stator, the tubular body being disposed around the rotor.

In another aspect of this embodiment, the housing defines a first axis, and wherein the tubular body is co-axial within the first-axis.

In another aspect of this embodiment, the rotor is an impeller, and wherein the impeller defines a plurality of hydrodynamic bearings.

In another aspect of this embodiment, during operation of the impeller, the impeller is maintained at predetermined radial distance from the tubular body, and wherein the predetermined radial distance is not uniform around the diameter impeller.

In another aspect of this embodiment, the stator is affixed within the inflow cannula at a predetermined radial distance from an interior surface of the housing, and wherein the predetermined radial distance is not uniform around the diameter of the stator.

In another aspect of this embodiment, the rotor defines a second axis parallel to the first axis.

In another aspect of this embodiment, the stator defines a third axis parallel to the first axis.

In another aspect of this embodiment, the first axis is parallel to the second axis.

In another aspect of this embodiment, the housing is sized to be inserted within a ventricle of a human heart.

In another embodiment, a blood pump includes a housing having an inflow cannula sized to be implanted with a human heart, the inflow cannula defining a proximal end, a distal end, and a first axis extending from the proximal end to the distal end. A ferromagnetic impeller is disposed within the housing proximate to the proximal end of the inflow cannula, the impeller defines a second axis and configured impel blood in a direction along the second axis. A stator is disposed within housing and around the ferromagnetic rotor, the stator being configured to apply a magnetic force causing rotation of the ferromagnetic impeller around the second axis, the stator defines a third axis offset from the second axis and offset from the first axis. A non-ferromagnetic tubular body is disposed within the housing and around the impeller, the tubular body being co-axial within the first axis.

In another aspect of this embodiment, the impeller defines a plurality of hydrodynamic bearings.

In another aspect of this embodiment, the blood pump further includes an epoxy disposed between an inner surface of the stator and the tubular housing, the epoxy being configured retain the stator in its eccentric position with respect to the inflow cannula.

In another aspect of this embodiment, during operation of the impeller, the impeller is maintained at predetermined radial distance from the tubular body, and wherein the predetermined radial distance is not uniform around the diameter impeller.

In another aspect of this embodiment, the tubular body is eccentric to the impeller creating a fluid gap between the impeller and the tubular body, the fluid gap being non-uniform around the impeller.

In another aspect of this embodiment, at least a portion of the stator is in contact with the tubular body.

In another aspect of this embodiment, the third axis parallel to the first axis.

In another aspect of this embodiment, the first axis is parallel to the second axis.

In another aspect of this embodiment, the second axis is parallel to the third axis.

In yet another embodiment, a blood pump includes a housing having an inflow cannula sized to be implanted with a human heart, the inflow cannula defining a proximal end, a distal end, and a first axis extending from the proximal end to the distal end. A ferromagnetic impeller defining a plurality of hydrodynamic bearings is disposed within the housing proximate to the proximal end of the inflow cannula, the impeller defining a second axis parallel to the first axis and configured impel blood in a direction along the second axis. A stator is disposed within housing and around the ferromagnetic rotor, the stator being configured to apply a magnetic force causing rotation of the ferromagnetic impeller around the second axis, the stator defining a third axis parallel to the second axis. A non-ferromagnetic tubular body is disposed within the housing and around the impeller, the tubular body being co-axial within the first axis, the tubular body being eccentric with the impeller and creating a fluid gap between the impeller and the tubular body, the fluid gap being non-uniform around the impeller.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
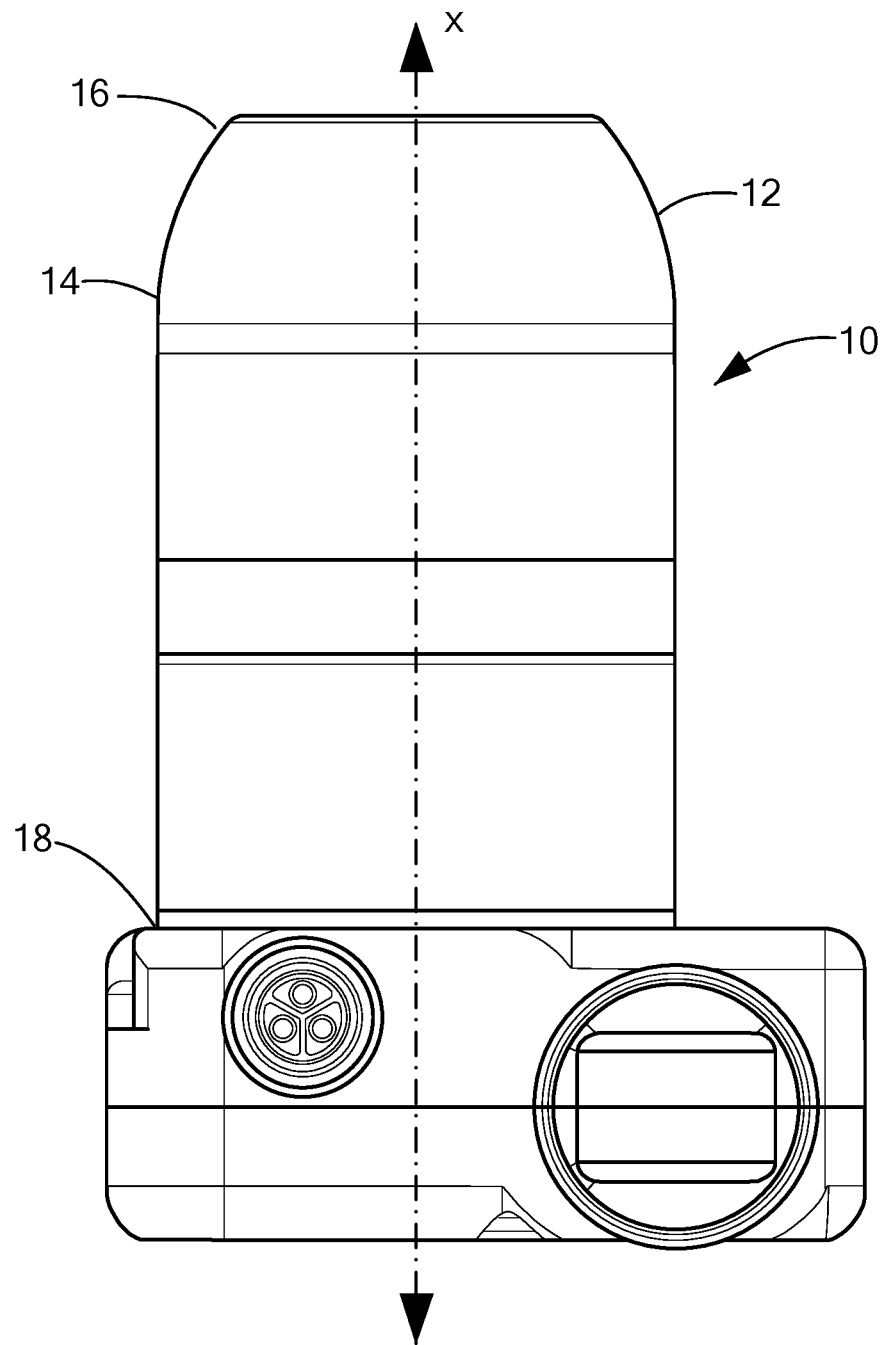
FIG. 1 is a side view of a blood pump according to one embodiment of the present application.

Now referring to the drawings in which like reference designators refer to like elements, there is shown in FIG. 1 an exemplary implantable blood pump constructed in accordance with the principles of the present application and designated generally as "10." The blood pump 10 includes a housing 12 configured to house the components of the blood pump. The housing 12 may be composed of biocompatible material and configured to be at least partially implanted within a human or animal's patient's heart. The housing 12 may further and inflow cannula 14 configured to be inserted within the heart, for example, the left or right ventricle. The inflow cannula 14 is configured to provide a fluid pathway for blood being pumped from the heart out through the blood pump 10 and out to the rest of the patient's circulatory system through an outflow cannula (not shown) in fluid communication with the inflow cannula 14. The housing 12 may define a first major longitudinal axis or housing axis ("x") extending from a distal end 16 configured to be positioned within the heart to a proximal end 18.

Figure 2:
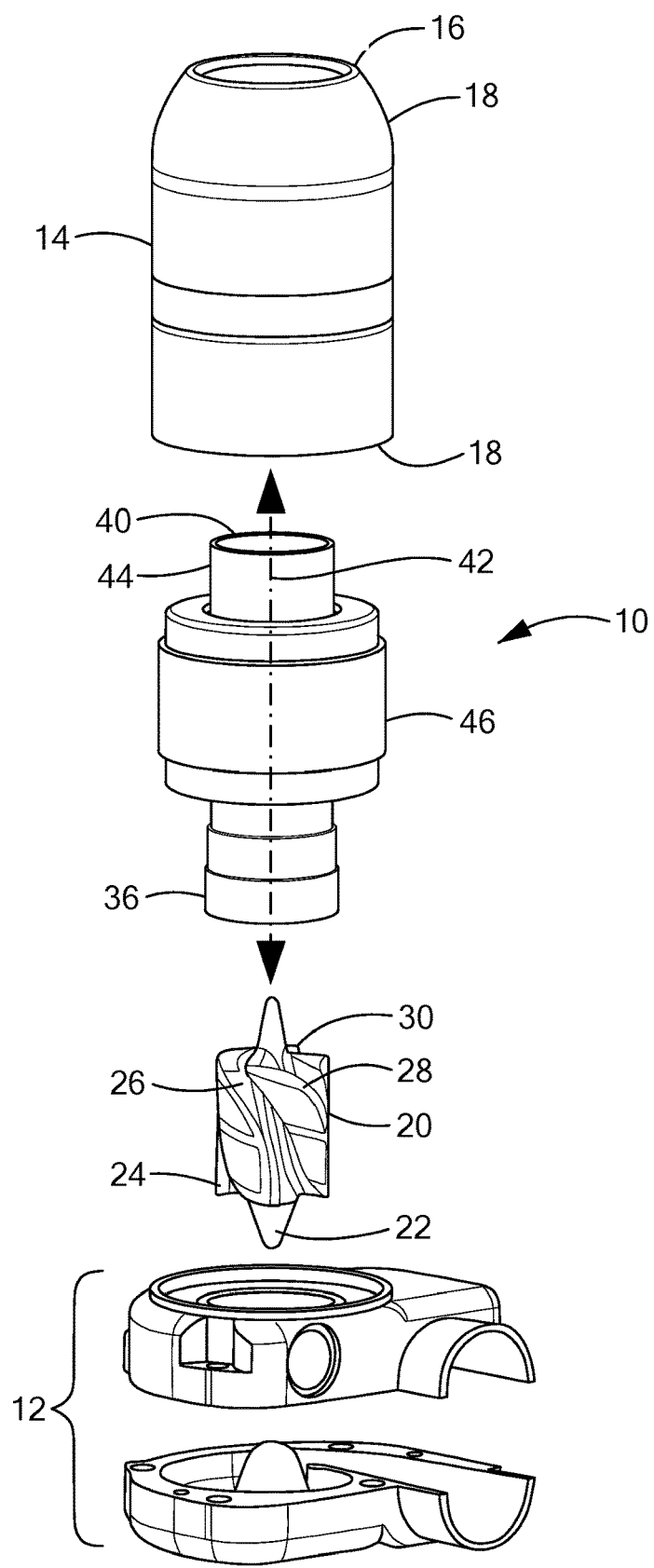
FIG. 2 is an exploded view of the blood pump shown in FIG. 1.
Figure 2A:
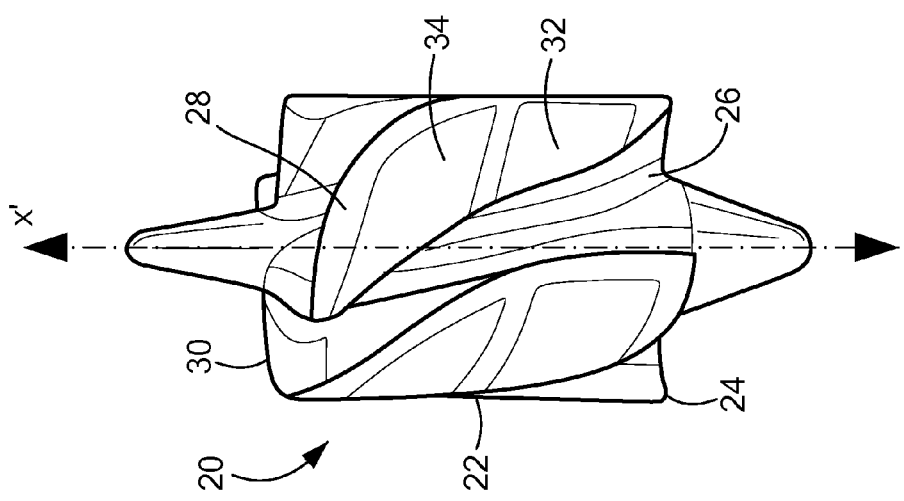
FIG. 2A is a zoomed in view of the rotor shown in FIG. 2.

Referring now to FIGS. 2 and 2A, disposed within the housing 12 is a ferromagnetic rotor 20 proximate to the proximal end 18 of the inflow cannula 14 and configured pump blood in a direction along the first axis toward an outlet. The rotor 20 may an axial flow impeller having a hub 22 defining a second major longitudinal axis or rotor axis x' about which the rotor is symmetric and parallel to the first major longitudinal axis x, but offset therefrom. The hub 22 includes plurality of blades 24 projecting from the hub 22. Each blade 24 may extend out of the hub 22 in an outward radial direction. The blades 24 are evenly spaced apart from one another circumferential around the hub 22 define a plurality of channels 26 through which blood flows axially. Each channel 26 is bounded by a forwardly facing surface of one blade 24 and a rearward facing surface of the next adjacent blade 24. Each blade 24 has a tip surface 28. Each tip surface 28 faces outwardly away from the second axis x' and defines the outermost extremity of the blade 24. Each tip surface 28 includes a land surface 30. Land surface 30 is in the form of a part of a surface of revolution around the second axis x'. In the particular embodiment depicted in FIG. 2, the surface of revolution is a circular cylinder, so that the radius from the second axis x' to land surface 30 is uniform over the entire extent of each land surface 30. Each tip surface 28 further includes hydrodynamic bearing surfaces 32 and 34. As best seen in FIG. 2, hydrodynamic bearing surface 32 is recessed radially from the land surface 30. The recess is at a maximum at the forward edge of the bearing surface of the blade 24. The recess depth diminishes progressively in the rearward circumferential direction, so that the bearing surface merges smoothly into the land surface 30 at the rearward edge of the bearing surface. The other hydrodynamic bearing surfaces of each blade 24 have a similar configuration. In the particular embodiment depicted, the forward edge of each bearing surface is recessed relative to the land area by about 0.0030 to 0.0040 inches, i.e., 0.076 to 0.010 mm. In this embodiment, the rotor 20 is formed from a solid piece of a ferromagnetic biocompatible alloy such as a platinum cobalt alloy. The material of rotor 20 is magnetized so as to provide permanent magnetic poles with polarization.

Figure 3:
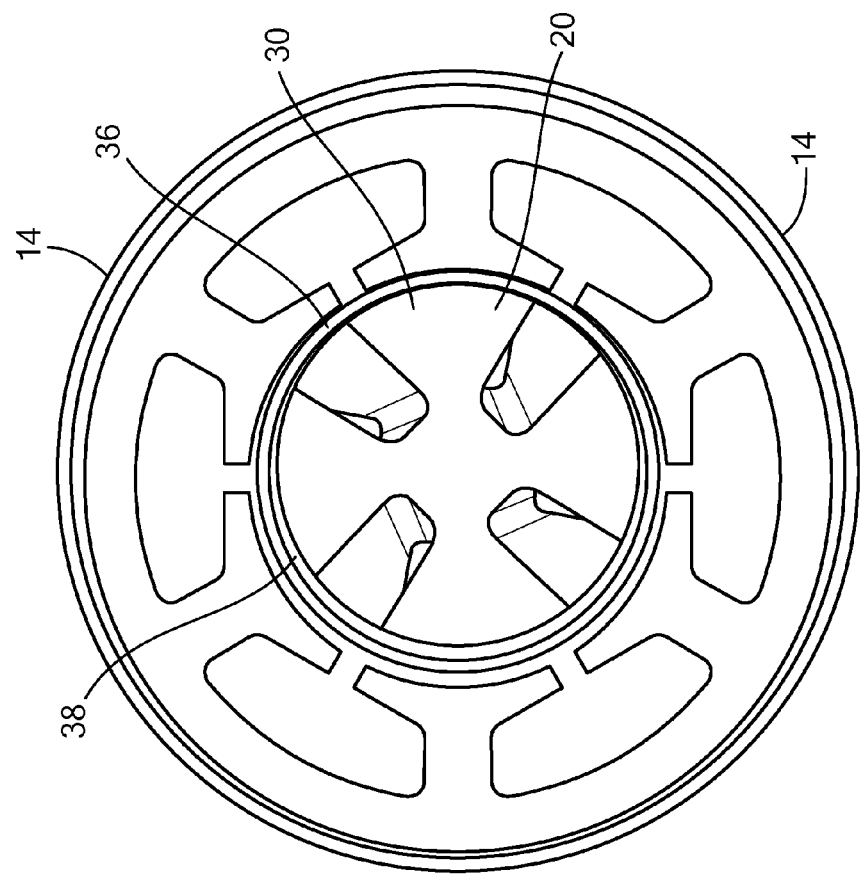
FIG. 3 is a cross-sectional view of the blood pump shown in FIG. 1 showing the eccentricity of the stator, tubular housing, and the rotor.

Referring now to FIGS. 1 and 3, the 10 pump further includes a tubular housing 36 formed from a non-magnetic material such as a ceramic disposed within the housing 12. Tubular housing 36 has an interior surface 38 defining a cylindrical bore 40. Bore 40 has a bore axis 42 that is co-axial with the first major longitudinal axis x. That is bore axis 42 and the first axis x are the same axis. The housing 36 also has a cylindrical exterior surface 44 concentric with the bore axis 42. Bore 40 has an internal diameter just slightly larger than the maximum diameter of rotor 20 defined by the land surfaces 30. For example, the bore diameter may be about 0.001-0.002 inches larger than the rotor diameter. When the second axis x' is concentric with the bore axis 42, there is a nominal radial clearance between the land surfaces 30 on the tips of the rotor blades 24 and the interior surface of the bore 40, such clearance being equal to the diameter of the bore minus the diameter of the rotor divided by two. For example, the diameter of the bore may be about 0.004 inches greater than the diameter of the rotor, so that the nominal radial clearance is about 0.002 inches. The second axis x' cannot be displaced from the bore axis 42 by more than the nominal radial clearance otherwise the rotor 20 is in direct contact with the interior surface 38 of the tubular housing 36 which would cause scratching of the tubular housing 36 and potentially thrombus. Rotor 20 is disposed in bore 40 with the second axis x' extending parallel with the bore axis 42 but offset therefrom.

Continuing to refer to FIG. 3, the pump 10 additionally includes a stator 46 fixed to the housing 36 and circumferentially surrounding the tubular housing 36 and the rotor 20. Stator 46 includes a ferromagnetic frame, which includes a large cylindrical element encircling the tubular housing 36 and pole pieces projecting inwardly from the circular element. The stator 46 is symmetrical about a third major longitudinal axis or stator axis x", the third axis x" being parallel to the first axis x and the second axis x' but offset from both axes respectively. The stator 46 in this embodiment further includes electrical coils surrounding each pole piece. A drive circuit (not shown) is connected to the various coils.

In operation, with the pump 10 is connected to a heart chamber or other source of blood, the drive circuit applies electrical currents through coils and varies these currents so as to create a continuously rotating magnetic field within bore 40. The rotating magnetic field spins the rotor 20 in the clockwise direction. As the rotor 20 spins, some blood passes between the hydrodynamic bearing 32 and 34 of the rotor 20 and the interior surface 38 of housing 36. The clockwise motion of the hydrodynamic bearing 32 and 34 relative to the interior surface 38 creates an increased pressure in the region between the hydrodynamic bearing surface 32 and the interior surface 38 of the housing 36 and thus creates a force on the rotor 22 in the radially inward direction, towards the rotor axis x'. These radial forces support the rotor out of contact with the interior surface 38 of the housing 36. Rotation of the rotor 20 in the clockwise direction causes the blades 24 of the rotor 20 to drive the blood in a downstream direction D relative to the rotor 20 and the housing 36. Magnetic interaction between the rotor and the ferromagnetic stator 46 may also exert axial forces, parallel to the bore axis 42, and maintain the axial position of the rotor 20 relative to the stator 46. The foregoing features and general mode of operation of the pump may be the same as those disclosed in U.S. Pat. No. 8,007,254 and U.S. Patent Application Publication No. 2015/0051438 A1, and used in axial flow blood pumps of the type sold under the designation MVAD by Heartware, Inc., assignee of the present application.

Figure 4:
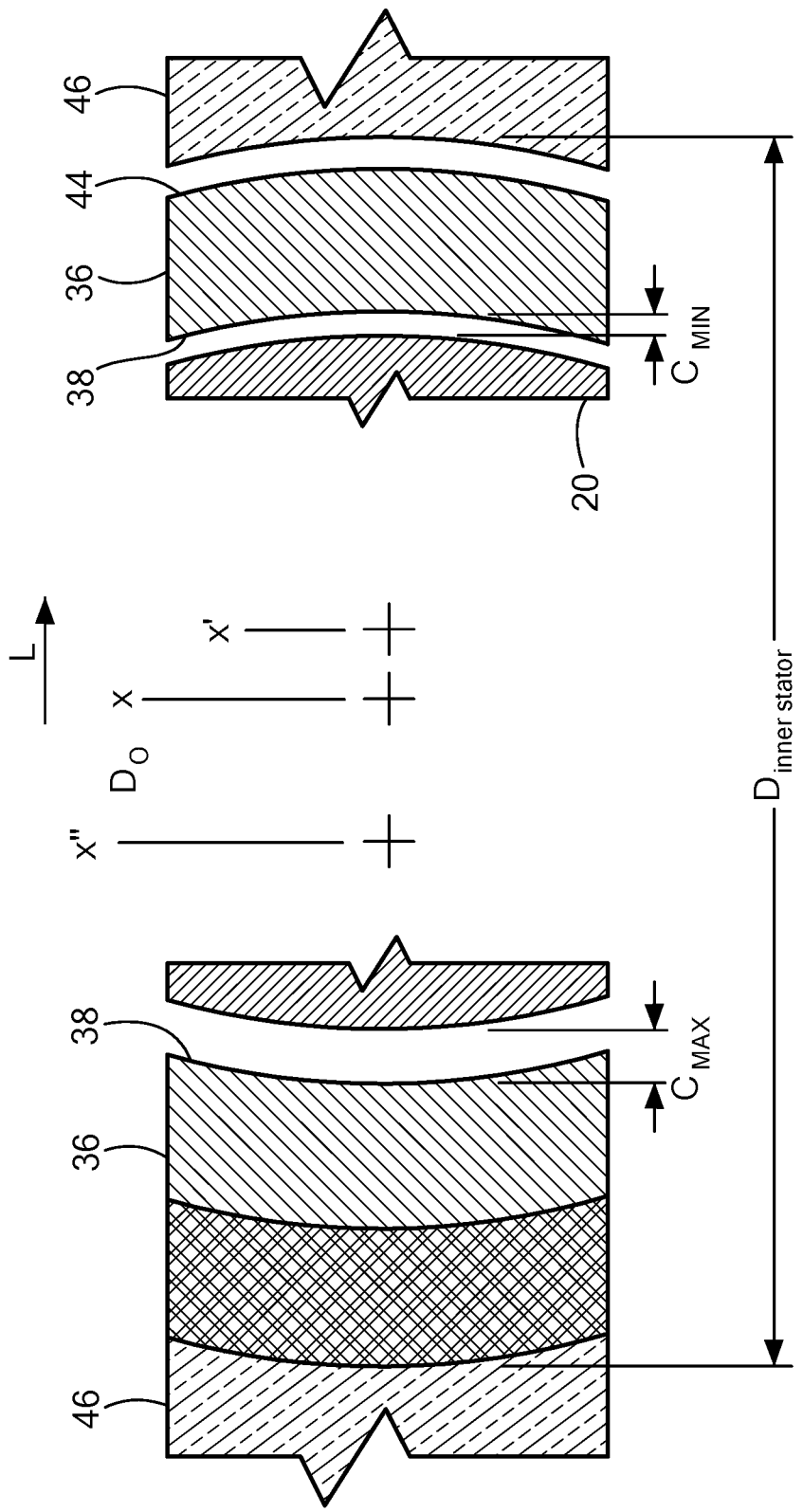
FIG. 4 is a diagrammatic view depicting spatial relationship of certain components used in the pump shown in FIG. 3.

Referring now to FIG. 4, the stator 46 has an inner diameter Dinner stator slightly larger than the outside diameter of housing 36. A small non-ferromagnetic shim, epoxy, or other adhesive material is interposed between the ferromagnetic frame or inner surface of the stator 46 and the exterior surface 44 of the tubular housing 36. Thus, the third axis x" or the stator axis is offset from the bore axis 42 in a direction parallel to the bore axis 42. This offset positions the ferromagnetic material of the frame closer to the bore axis 42 on the opposite side of the bore 40. Thus, the attraction between the permanent magnetic poles of the rotor 20 and the stator 46 are stronger in the lateral direction L (to the right in FIG. 4), opposite to the direction of the offset of the third axis x". The magnetic interaction between the rotor 20 and the stator 46 thus applies a force in the lateral direction L to the rotor 20, and tends to displace the rotor in the lateral direction L relative to housing 36 in the lateral direction. This tendency is resisted by the hydrodynamic bearings 32 and 34. As the rotor 20 moves closer to the interior surface 38 of the housing 36 on the right side as seen in FIG. 4, the clearance C between the rotor 20 and the interior surface 38 diminishes, and the radial force provided by the hydrodynamic bearings 32 and 34 on this side increases. The opposite effect occurs on the left side as seen in FIG. 4. The rotor comes to equilibrium at a position as indicated in FIG. 4, with the rotor axis or second axis x' offset from the bore axis 42, the first axis x, and the stator axis x" in the lateral direction L, but not touching the interior surface 38 of the housing 36. In another words, the stator 46 is eccentric with respect to the housing 12 and eccentric with respect to the rotor 20.

As the rotor 20 turns, the tip surface 28 of each blade 24 will passes to the interior wall 38 of the housing 36 on one side (to the right in FIG. 4) and further from the interior wall 387 on the opposite side (to the left in FIG. 4). Thus, the clearance between the land surface 30 and the interior surface 38 is at a minimum $C_{MIN}$ when a particular blade 24 is on the right side in FIG. 4 and at a maximum $C_{MAX}$ when the blade is on the left side. Stated another way, the hydrodynamic bearings 32 and 34 defined by each blade 24 and the interior surface 38 of the housing 36 operates with a small clearance and with a larger clearance. This action helps to keep the hydrodynamic bearings 32 and 34 free of thrombus and other deposits. Although the present disclosure is not limited by any theory of operation, it is believed that any thrombus or other deposit which may become trapped between these surfaces when the clearance is small will be washed away by the blood when the clearance is larger.

As discussed above, the rotor axis x' can be displaced from the bore axis 42 by at most the nominal clearance. During startup, when the hydrodynamic bearings 32 and 34 are inactive, the rotor axis x' may be displaced in any direction relative to the bore axis 42. To assure that the stator frame has a greater magnetic attraction for the rotor 20 in the lateral direction L (to the right in FIG. 4) even if the rotor is momentarily displaced to the opposite direction (to the left in FIG. 4), the offset distance $D_O$ should be greater than the nominal clearance, i.e., greater than the diameter of the bore minus the diameter of the rotor divided by two. For even greater assurance, the offset distance $D_O$ may be several times by the nominal clearance. In the particular embodiment discussed above, $D_O$ may be about 0.004-0.012 inches.

The features described above may be varied. For example, in other embodiments the stator frame may be asymmetrical. For example, if one or more of the pole pieces on the right side of the bore axis 42 and stator axis x" is made wider than the pole pieces on the left side, the magnetic interaction between the poles of the rotor 20 and the frame may apply a force to the rotor directed to the right. In the embodiments discussed above, the currents applied through the coils produce magnetic fields which are symmetrical with respect to the bore axis 42. Thus, the lateral force on the rotor 20 applied by magnetic interaction between the rotor 20 and a coil on one side is balanced by an oppositely-directed lateral force applied by interaction with a coil on the opposite side. In other embodiments, the magnetic fields applied by the coils may be imbalanced so that the coils as a whole apply a magnetic force to the rotor in a lateral direction. For example, the currents passing through one or more of the coils may be modulated in synchronism with rotation of the rotor 20 by the drive circuit so that the coils 90 on one side of the housing 36 exert a stronger magnetic attraction for the poles which are momentarily disposed on that side of the housing 36. The modulated current is superimposed on the symmetrical current used to generate the rotating magnetic field. In a further variant, additional windings can be provided in coils on one side. In yet another variant, separate coils (not shown) may be provided to carry the modulated current. Where the lateral force is provided by modulated currents, the modulation can be varied with time so that the lateral force is provided in a lateral direction which rotates with time. This causes the rotor axis x' to be displaced from the bore axis 42 in a direction which varies with time. Such variation with time desirably is at a speed different from, and desirably much slower than, the rotational speed of the rotor.

In the embodiments above, the lateral force applied to the rotor 20 stabilizes the rotor against whip. Whip, as referred to herein, is a condition in which the rotor axis x' becomes offset from the bore axis 42 and rotates around the bore axis 42. The additional stability afforded by the lateral force can allow a pump with a greater nominal clearance to operate without whip. This in turn can further alleviate accumulation of thrombus or other particles in the hydrodynamic bearings. As these and other variations and combinations of the features discussed above may be utilized, the foregoing description of certain embodiments should not be taken as limiting the invention.

What is claimed is:

1. A blood pump, comprising:
   a housing defining a proximal end, a distal end, and a first axis extending from the proximal end to the distal end;
   a ferromagnetic rotor disposed within the housing and configured pump blood in a direction along the first axis; and
   a single stator disposed within housing and around the ferromagnetic rotor, the stator being configured to apply a magnetic force causing rotation of the ferromagnetic rotor;
   a non-ferromagnetic tubular body disposed between the rotor and the stator and co-axial with the first axis, the rotor being entirely disposed within the non-ferromagnetic tubular body the stator being affixed within the housing at a predetermined non-uniform radial distance from an exterior surface of the tubular body to an inner diameter of the stator;
   and during operation of the blood pump, the rotor is maintained at a predetermined non-uniform radial distance from the tubular body and the stator is eccentric to the rotor.

2. The blood pump of claim 1, wherein the rotor is an impeller, and wherein the impeller defines a plurality of hydrodynamic bearings.

3. The blood pump of claim 1, wherein the rotor defines a second axis parallel to the first axis.

4. The blood pump of claim 3, wherein the stator defines a third axis parallel to the first axis.

5. The blood pump of claim 4, wherein the first axis is parallel to the second axis.

6. The blood pump of claim 1, wherein at least a portion of the housing is sized to be inserted within a ventricle of a human heart.

7. A blood pump, comprising:
   a housing having an inflow cannula sized to be implanted with a human heart, the inflow cannula defining a proximal end, a distal end, and a first axis extending from the proximal end to the distal end;
   a ferromagnetic impeller disposed within the housing proximate to the proximal end of the inflow cannula, the impeller defining a second axis and configured impel blood in a direction along the second axis; and
   a single stator disposed within housing and around the ferromagnetic impeller, the stator being configured to apply a magnetic force causing rotation of the ferromagnetic impeller around the second axis, and during use, the stator defines a third axis offset from the second axis and offset from the first axis; and
   a non-ferromagnetic tubular body disposed within the inflow cannula and around the impeller, the tubular body being co-axial within the first axis, the stator being affixed within the housing at a predetermined non-uniform radial distance from an exterior surface of the tubular body to an inner diameter of the stator.

8. The blood pump of claim 7, wherein the impeller defines a plurality of hydrodynamic bearings.

9. The blood pump of claim 7, wherein the blood pump further includes an epoxy disposed between an inner surface of the stator and the tubular body, the epoxy being configured retain the stator in an eccentric position with respect to the inflow cannula.

10. The blood pump of claim 7, wherein during operation of the impeller, the impeller is maintained at predetermined radial distance from the tubular body, and wherein the predetermined radial distance is not uniform around the diameter impeller.

11. The blood pump of claim 7, wherein the tubular body is eccentric to the impeller creating a fluid gap between the impeller and the tubular body, the fluid gap being non-uniform around the impeller.

12. The blood pump of claim 7, wherein at least a portion of the stator is in contact with the tubular body.

13. The blood pump of claim 7, wherein the third axis parallel to the first axis.

14. The blood pump of claim 7, wherein the first axis is parallel to the second axis.

15. The blood pump of claim 7, wherein the second axis is parallel to the third axis.

16. A blood pump, comprising:
   a housing having an inflow cannula sized to be implanted with a human heart, the inflow cannula defining a proximal end, a distal end, and a first axis extending from the proximal end to the distal end;
   a ferromagnetic impeller defining a plurality of hydrodynamic bearings disposed within the housing proximate to the proximal end of the inflow cannula, the impeller defining a second axis parallel to the first axis and configured impel blood in a direction along the second axis;
   a single stator disposed within housing and around the ferromagnetic rotor, the stator being configured to apply a magnetic force causing rotation of the ferromagnetic impeller around the second axis, and during use, the stator defines a third axis parallel to the second axis; and
   a non-ferromagnetic tubular body disposed within the inflow cannula, the impeller being disposed within and surrounded by the non-ferromagnetic tubular body, the tubular body being co-axial within the first axis, and during use, the tubular body being eccentric with the impeller and creating a fluid gap between the impeller and the tubular body, the fluid gap being non-uniform around the impeller, the stator being affixed within the housing at a predetermined non-uniform radial distance from an exterior surface of the tubular body to an inner diameter of the stator.

* * * * *